United States Patent [19]
Vergano et al.

[11] Patent Number: 5,709,665
[45] Date of Patent: Jan. 20, 1998

[54] APPARATUS AND METHOD FOR HOLDING MEDICAL CONDUITS

[75] Inventors: Egidia M. Vergano, Los Altos, Calif.; Ronald D. Russo, Barrington, R.I.

[73] Assignee: Dale Medical Products, Inc., Plainville, Mass.

[21] Appl. No.: 658,363

[22] Filed: Jun. 5, 1996

[51] Int. Cl.[6] ............................................. A61M 5/32
[52] U.S. Cl. ..................... 604/174; 604/179; 604/180; 128/DIG. 26
[58] Field of Search ........................... 604/174, 179, 604/180; 128/DIG. 26

[56] References Cited

U.S. PATENT DOCUMENTS

| | | | |
|---|---|---|---|
| 3,146,778 | 9/1964 | Krawiec | 128/DIG. 26 X |
| 3,826,254 | 7/1974 | Mellor | 604/180 |
| 4,074,397 | 2/1978 | Rosin | 24/73 |
| 4,122,857 | 10/1978 | Haerr | 604/180 |
| 4,308,642 | 1/1982 | Heyman | 24/306 |
| 4,457,754 | 7/1984 | Buttaravoli | 604/180 |
| 4,534,762 | 8/1985 | Heyer | 604/180 |
| 4,583,976 | 4/1986 | Ferguson | 128/DIG. 26 X |
| 4,639,980 | 2/1987 | Peterson | 24/306 |
| 4,706,914 | 11/1987 | Ground | 248/74.3 |
| 4,707,906 | 11/1987 | Posey | 29/453 |
| 4,988,338 | 1/1991 | Taylor et al. | 604/180 |
| 5,037,397 | 8/1991 | Kalt et al. | 604/174 |
| 5,098,399 | 3/1992 | Tollini | 604/180 |
| 5,100,393 | 3/1992 | Johnson | 604/180 |
| 5,167,050 | 12/1992 | Korsen | 24/16 R |
| 5,200,245 | 4/1993 | Brodrick, Jr. | 428/100 |
| 5,451,725 | 9/1995 | Goldman | 181/131 |

OTHER PUBLICATIONS

"Dale® Hug Hospital Utility Grip," by Dale Medical Products, Inc., Jul. 1990.

*Primary Examiner*—Sam Rimell
*Assistant Examiner*—Robert W. Racunas
*Attorney, Agent, or Firm*—Wolf, Greenfield & Sacks, P.C.

[57] ABSTRACT

A disposable device and method for holding a plurality of medical conduits including an elongated foam strip having first and second ends and a layer of repositionable adhesive on a first surface of the strip. A clip is provide at the first end for releasably attaching the device to a bed sheet, blanket or patient's clothing, and the second end is folded over toward the first end with the conduits secured between the layers by the adhesive layer which substantially surrounds the circumference of each conduit to hold the same without allowing the conduits to be twisted or pulled through the holder.

20 Claims, 3 Drawing Sheets

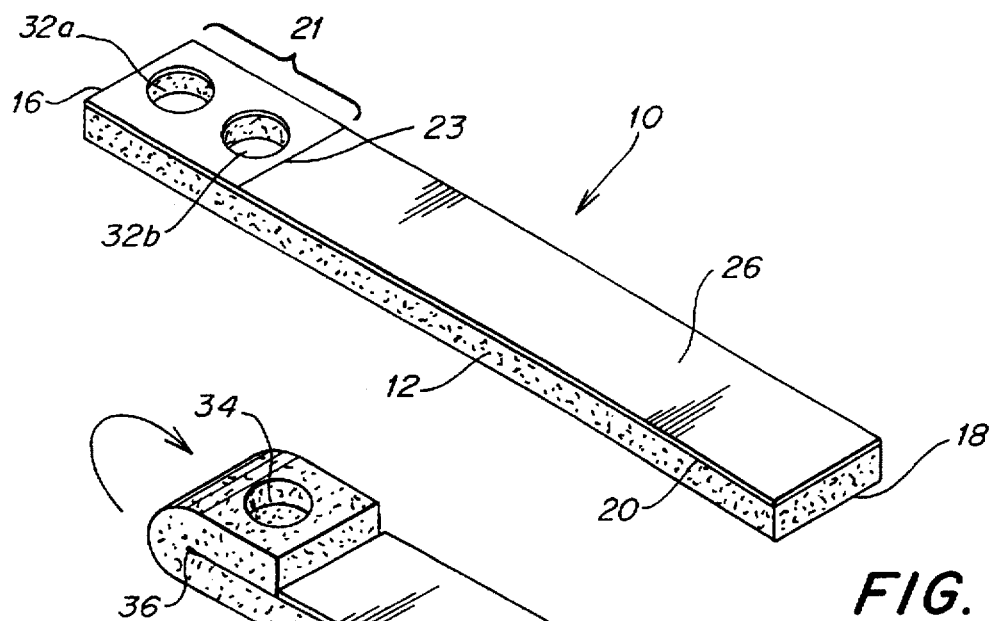
FIG. 1
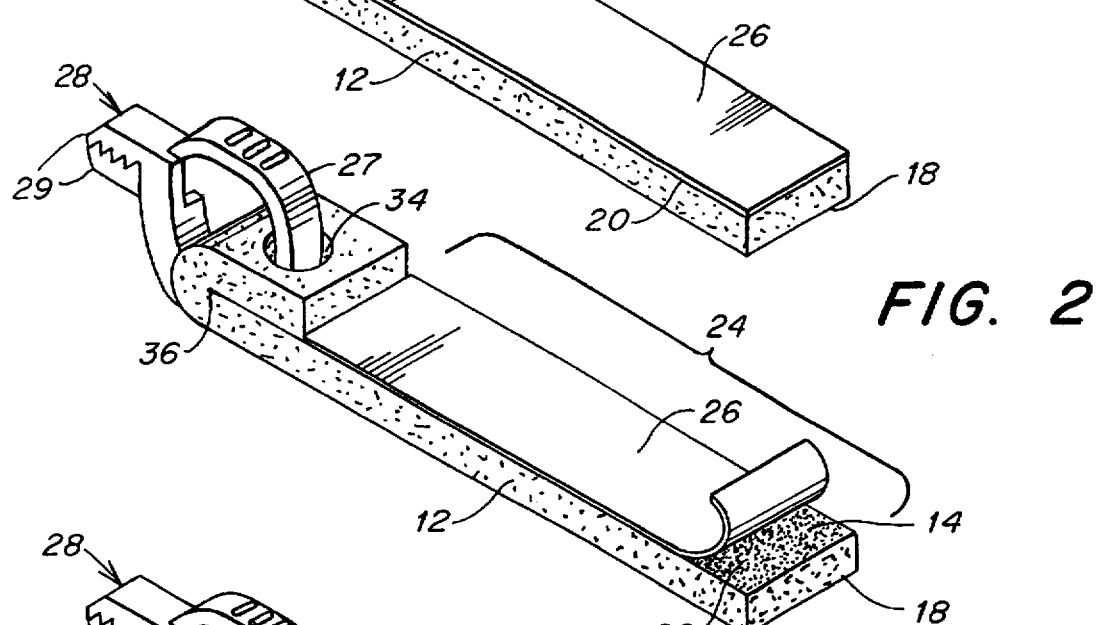
FIG. 2
FIG. 3
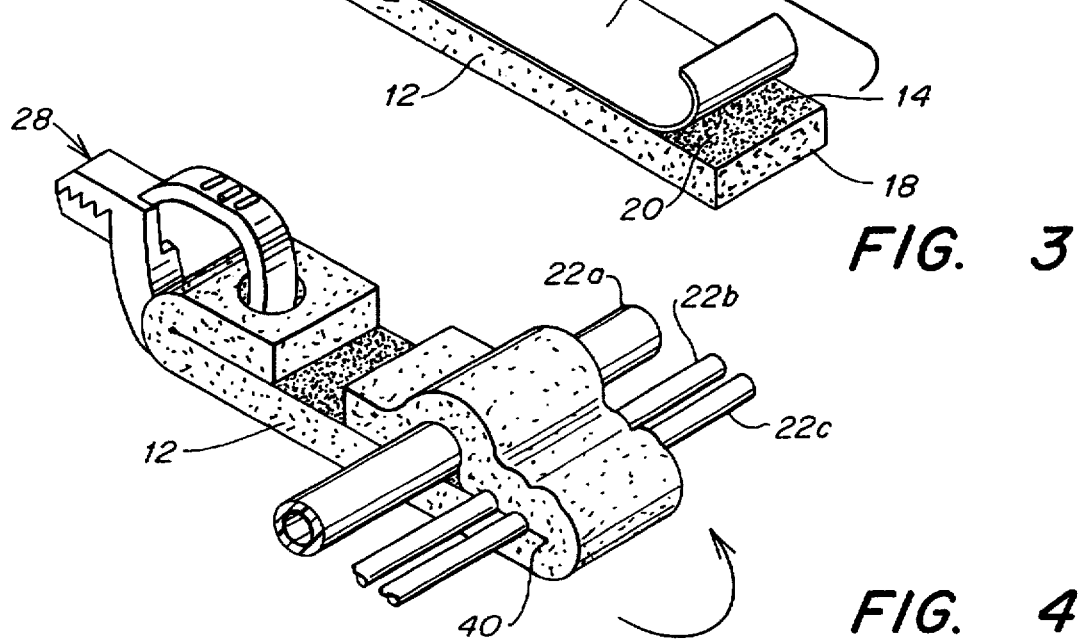
FIG. 4

APPARATUS AND METHOD FOR HOLDING MEDICAL CONDUITS

FIELD OF THE INVENTION

This invention relates to the field of medical devices and more particularly to a disposable apparatus and method for holding conduits, such as medical tubes and the like, in a repositionable and secure manner.

BACKGROUND OF THE INVENTION

In the medical field it is often necessary to clamp external tubes and conduits to a patient's body. These tubes and conduits include feeding tubes, nasogastric tubes, chest tubes, catheter tubes, dialysis and angiocath tubes, ventilator circuit tubing, and other conduits for introducing fluids intravenously or through the nose or mouth of the patient. Several prior art devices are known for clamping the tubes to the body or the area surrounding the patient.

U.S. Pat. No. 4,074,397 to Rosin which issued Feb. 21, 1978, discloses a disposable tube holder comprising a thin flexible pad with a pressure sensitive adhesive layer on one side for removable attachment to a sheet or a bed rail. The pad has an elongated flexible strip depending therefrom with hook/loop fastener material attached to a free end of the strip, wherein the strip is wrapped around a tube or cord and the hook/loop fastener element impressed upon the pad.

U.S. Pat. No. 4,308,642 to Heyman which issued Jan. 5, 1982, discloses a device for holding medical conduits in a hospital setting. The device comprises a generally flat flexible fabric pad having a metal clip at one end for securing the pad to a bed sheet or hospital gown. A tab extends across one surface of the pad, such that the conduit(s) can be secured between the tab and the pad. The adjoining surfaces of the tab and pad have hook and loop fastener material so that the tab can be easily removed from and secured to the pad. The pad is made of a washable fabric and the device is reusable.

U.S. Pat. No. 4,639,980 to Peterson which issued Feb. 3, 1987, discloses a tube organizer for hospital use which has separate hook and loop straps joined by stitching or metal eyelets, and a stainless steel clip for attachment to a bed. The reusable device is made from materials designed to withstand high temperature sterilization.

U.S. Pat. No. 5,037,397 to Kalt et al. which issued Aug. 6, 1991, discloses a clamp for holding a medical tube comprising a base with adhesive for securing the base to a patient's face, and a flap for engaging the tube which is formed separately from the base. The flap and base have hook and loop fasteners for releasable engagement and adhesive surfaces for adhering the tube therebetween.

SUMMARY OF THE INVENTION

A disposable device and method for holding one or more medical conduits or tubes (collectively "conduits") is described. The device comprises a strip of flexible material which has a first surface and first and second ends. There is an attachment mechanism at is the first end for attaching the device to a sheet, blanket or hospital gown. The flexible strip is adapted to be folded and doubled over from the second end so that an adhesive layer on the first surface substantially surrounds the exposed circumference of each conduit. The adhesive layer can be located on substantially all of the first surface, or in alternative embodiments may be located on one or both of a central part and a distal part (extending from the second end) of the first surface.

BRIEF DESCRIPTION OF THE DRAWINGS

FIG. 1 is a top perspective view of a tube holder according to a first embodiment of the present invention, having adhesive on all of an upper first surface and two die cut holes at the first end.

FIG. 2 shows the holder of FIG. 1 but with the first end folded over to align the two holes and form a through hole at the first end of the strip.

FIG. 3 shows the holder of FIG. 2 with a plastic clip disposed through the aligned holes in the first end and a portion of the liner paper pulled back at the second end.

FIG. 4 shows the holder in use, wherein the second end is folded back over to secure a plurality of conduits.

DETAILED DESCRIPTION

Figure 5:
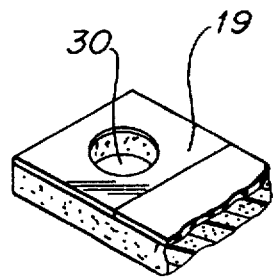
FIG. 5 is a partial perspective view of an alternative first end embodiment with one hole surrounded by a reinforcing film.

FIGS. 1–4 show a first embodiment of a disposable medical device tube holder 10 according to the present invention. It is designed for use in a hospital setting, where many conduits and tubes are attached to a patient as he/she lies in bed. There is a need for these tubes to be secure, i.e., not able to be twisted or pulled through the holder, but also for the holder to allow easy positioning and repositioning. The device should be inexpensive to manufacture and yet maintain its gripping power when exposed to fluids. The medical tube holder 10 of the present invention accomplishes these objects.

The holder 10 comprises a generally flat and flexible strip of material 12 having a first upper surface 14, a first end 16 and an opposing second end 18. A repositionable adhesive layer 20 is located on the entire first surface 14. The second end 18 of the strip is adapted to be doubled over toward the first end 16 so that the adhesive layer 20 substantially surrounds the exposed circumference of the each conduit to secure the same between the doubled over strip. The strip 12 can be made of a closed cell or an open cell foam layer, such as a polyethylene cross-linked foam, which is prefabricated and die cut. In this example, the dimensions of the strip are approximately six to eight inches in length, one inch in width, and one eighth to one quarter inch in thickness. The strip may be dimensioned to accept larger diameter tubes, such as breathing circuit tubes.

A releasable liner 26, made of coated paper, covers the first surface 14 and is removable. The liner is separable at a score line 23 which defines a proximal portion 21 of the strip adjacent the first end 16 having two die cut holes 32a and 32b. Referring to FIG. 2, it is shown how the proximal portion 21 is folded in half along fold line 36 so that the two die cut holes 32a and 32b are aligned to form one reinforced through hole 34. By pressing the folded portion together, the two die cut holes are held together by the adhesive layer 20 to form the one through hole 34.

Referring to FIG. 3, there is shown the device 10 with a molded plastic clip 28 passing through the hole 34 in the proximal portion. The clip has a ring 27 at one end passing through hole 34 and two opposed clamping jaws 29 at the other end. By pressing the ring between two fingers, the jaws are opened. The jaws are designed to releasably secure the device to a bed sheet, blanket or to the clothing of the patient.

The liner 26 which covers the adhesive layer 20 is partially removed in FIG. 3. The adhesive is accessible in a combined central and distal portion 24 of the first surface 14 (extending from the second end 18). The liner 26 may extend past either or both of ends 16 and 18 to form a tab for easier removal from the adhesive surface 20.

FIG. 4 shows the device 10 in use. The top release liner 26 has been removed from the first surface 14 exposing the adhesive 20. Several conduits 22a, 22b and 22c have been placed on the adhesive on the central portion of the strip, and the distal portion of the strip is then doubled over at a user determined bend location 40 so that the distal portion of the strip lies over the central portion (and tubes). The adhesive layer 20 thereby contacts itself, at either side of each tube, and attaches to itself in its doubled over position thereby securing conduits 22a, 22b and 22c. The adhesive layer 20 substantially surrounds the exposed circumferences of the conduits 22 to prevent twisting and pulling through of the conduits; the bottoms of the conduits are further held by the adhesive on the central portion of the strip. The adhesive layer is a "repositionable" adhesive which releasably secures the conduits and the folded over portion to enable adjustment and removal of the tubes; a suitable adhesive is Avery Fast Tape 8306, available from Avery Dennison Specialty Tape Division, Painesville, Ohio.

Figure 6:
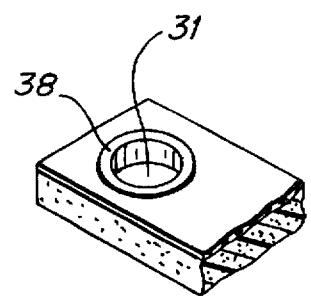
FIG. 6 is a partial perspective view of another first end embodiment with one hole reinforced by a metal grommet.

Referring to FIGS. 5 and 6, there are shown proximal portions of two alternative embodiments. In FIG. 5, a proximal portion 19 at the first end of the strip has a single hole 30 and is reinforced with a polyester film material having a thickness of 1–10 mil. In FIG. 6, a single hole 31 is reinforced with a metal grommet 38, which may be nickel plated or brass.

Figure 7:
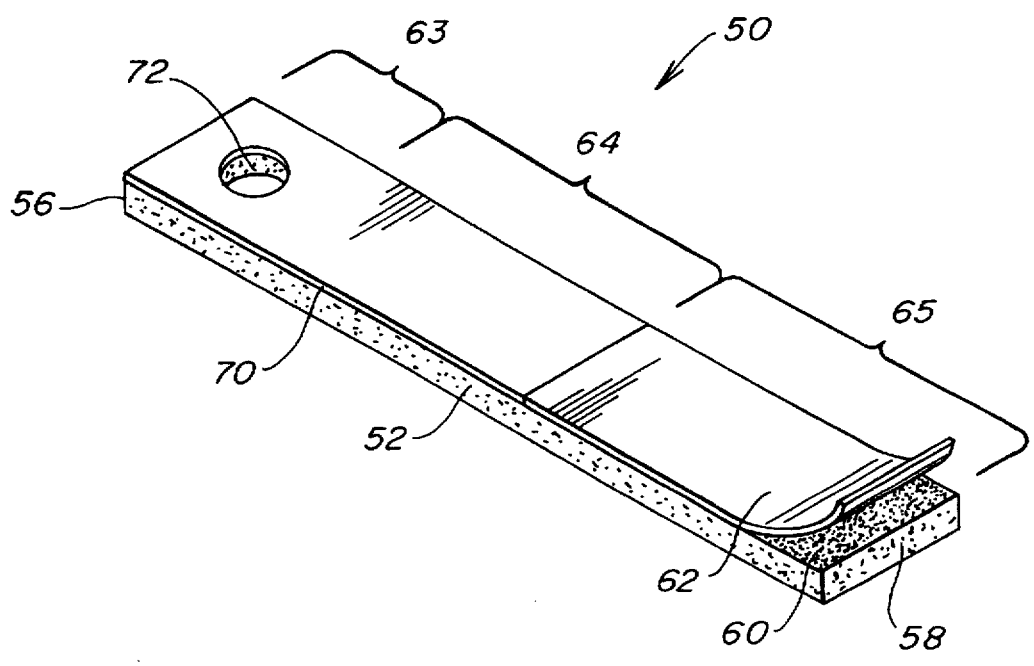
FIG. 7 is a top perspective view of a further alternative embodiment having a target material in a central portion of the strip and adhesive in a distal portion (extending from the second end).

Referring to FIG. 7, there is shown another embodiment of the present invention. The device 50 comprises a strip 52 having a first end 56, a second end 58, and extending from the second end a distal portion 65 covered by an adhesive layer 60 and a liner paper 62. The strip 52 can be a die-cut strip of cross-linked polyethylene foam with a top release liner paper 62. The strip 52 may be approximately seven inches long, one inch wide and an eighth to a quarter of an inch thick. Both a proximal portion 63 and a central portion 64 have a nonadhesive material 70 disposed thereon, which may occupy approximately 4 inches of the strip. The material 70 is a reinforced polyester plastic film or other suitable material sealed or mounted to the strip 52. The polyester film may have the ability to be printed on. At the proximal portion, the material 70 reinforces the hole 72. At the central portion 64, the material 70 forms a target material to which the distal adhesive portion 65 is releasably attachable. In use, the liner paper 62 is removed from the distal portion 65 to expose the adhesive 60 below. The conduits 22a, 22b and 22c are placed on the central portion 68 and the distal portion 66 is bent or folded over, thereby substantially surrounding and securing the conduits with the adhesive 60. An attachment member is positioned through the hole 72 for attaching the strip 52 to a sheet, etc., by means of a clip.

Alternatively, in another embodiment the adhesive/target portions could be reversed such that central portion 64 was adhesive and distal portion 65 was nonadhesive.

Figure 8:
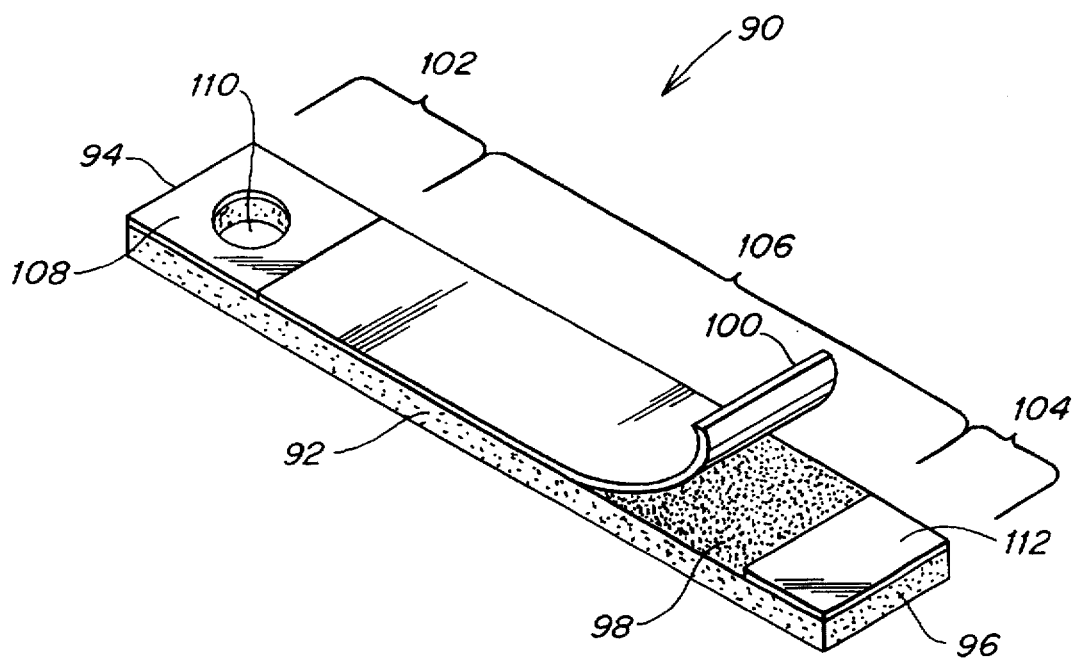
FIG. 8 is a top perspective view of another alternative embodiment having a tab at the second end and adhesive in the central portion.
Figure 9:
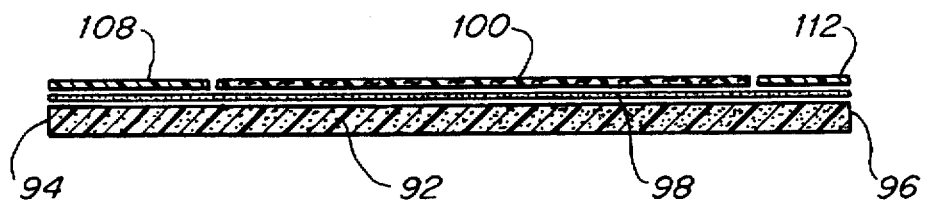
FIG. 9 is a cross-sectional view of the device of FIG. 8.

Referring to FIGS. 8–9, there is shown another alternative embodiment. The device 90 comprises a strip 92 of a foam material 93 having a first end 94 and a second end 96 with a repositional adhesive layer 98 disposed across the entire upper surface of the foam. A proximal portion 102 adjacent the first end has a nonadhesive material 108 disposed over the adhesive and foam, such as a polyester film, and through hole 110. A distal portion 104 adjacent the second end also has a nonadhesive material 112, such as polyester film, disposed over the adhesive and foam. Between the proximal portion 102 and the distal portion 104 there is a central portion 106 covered by a releasable liner 100, over the adhesive layer 98.

The distal nonadhesive surface 112 forms a tab which makes it easier to separate the folded over portion from the repositional adhesive 98 in the central portion for removal and/or repositioning of the conduits. Both polyester surfaces 108, 112 may be capable of receiving printed information, as well as the adhesive surface 98.

In use, the liner 100 is removed from the central portion 106 to expose the adhesive layer 98 below. Conduits are placed on the central portion 106 and the strip is folded over (from the second end) so that adhesive layer 98 substantially surrounds and secures the conduits therebetween.

Further modifications will occur to those skilled in the art and are deemed to be within the scope of the invention as defined by the following claims.

We claim:

1. A device for holding at least one conduit comprising:
   an elongated flexible strip of material having a first surface, a second surface, and first and second ends, the strip including:
      a proximal portion extending from the first end;
      a distal portion extending from the second end; and
      a central portion between the proximal and distal portions;
   an attachment mechanism secured to the proximal portion for attaching the device to a sheet material;
   a repositionable adhesive layer on the first surface extending over at least one of the central and distal portions; and
   a second, non-adhesive surface on the second surface, opposite the repositionable adhesive layer;
   wherein the second end of the strip is doubled over toward the first end so as to form an enclosed end including a user determined bend location, and wherein the distal portion of the strip lies substantially over the central portion such that the second end of the strip remains readily accessible for repositioning of the distal portion, with the adhesive layer substantially surrounding the at least one conduit to secure the conduit in position between the doubled over strip.

2. The device of claim 1, wherein the adhesive layer is on both the central and distal portions of the strip.

3. The device of claim 1, wherein the adhesive layer is on the distal portion of the strip and a nonadhesive layer is on the central portion of the strip.

4. The device of claim 1, wherein the adhesive layer is on the central portion of the strip and a nonadhesive layer is on the distal portion of the strip.

5. The device of claim 1, wherein the proximal portion of the strip is reinforced.

6. The device of claim 5, wherein the proximal portion is doubled over.

7. The device of claim 5, wherein a plastic film reinforces the proximal portion.

8. The device of claim 1, wherein the proximal portion includes at least one hole through which the attachment mechanism is disposed.

9. The device of claim 8, wherein a grommet reinforces the at least one hole.

10. The device of claim 1, wherein the attachment mechanism includes a clip.

11. The device of claim 1, wherein a releasable liner covers the adhesive layer.

12. The device of claim 1, wherein a tab is provided in the distal portion to facilitate repositioning of the doubled over strip.

13. The device of claim 1, wherein the adhesive layer contacts itself on either side of the at least one conduit.

14. The device of claim 1, wherein the adhesive layer lies substantially over a plurality of conduits.

15. A device for holding at least one conduit comprising:
   an elongated flexible strip of foam material having a first surface, a second surface, and first and second ends, the strip including:
     a proximal portion extending from the first end;
     a distal portion extending from the second end; and
     a central portion between the proximal and distal portions;
   an attachment mechanism secured to the proximal portion for attaching the device to a sheet material;
   a repositionable adhesive layer on the first surface extending over at least one of the central and distal portions; and
   a second, non-adhesive surface on the second surface, opposite the repositionable adhesive layer;
   wherein the second end of the strip is configured and arranged to be doubled over toward the first end so as to form an enclosed end including a user determined bend location, and wherein the distal portion of the strip lies substantially over the central portion such that the second end of the strip remains readily accessible for repositioning of the distal portion, with the adhesive layer substantially surrounding the at least one conduit to secure the conduit in position between the doubled over strip.

16. A method for holding at least one conduit comprising:
   providing an elongated flexible strip of material having a first surface and first and second ends, the strip including:
     a proximal portion extending from the first end;
     a distal portion extending from the second end; and
     a central portion between the proximal and distal portion;
   an attachment mechanism secured to the proximal portion;
   a repositionable adhesive layer on the first surface extending over at least one of the central and distal portions; further comprising the steps of:
     securing the attachment mechanism to a sheet material;
     positioning the at least one conduit on the first surface in the central or distal portion and doubling over the second end of the strip toward the first end so that an enclosed end including a user determined bend location is formed, with the distal portion of the strip lying substantially over the central portion, and the second end of the strip remaining readily accessible for repositioning of the distal portion, with the adhesive layer substantially surrounding the at least one conduit to secure the conduit in position between the doubled over strip.

17. The method of claim 16, wherein the adhesive layer is on both the central and distal portions of the strip, the at least one conduit is positioned on the central portion, and the distal portion is positioned over the central portion in the doubled over strip.

18. The method of claim 16, wherein the adhesive layer is on the distal portion of the strip and a nonadhesive layer on the central portion of the strip, the at least one conduit is positioned on the central portion, and the distal portion is positioned over the central portion in the doubled over strip.

19. The method of claim 16, wherein the adhesive layer is on the central portion of the strip and a nonadhesive layer on the distal portion of the strip, the at least one conduit is positioned on the central portion, and the distal portion is positioned over the central portion in the doubled over strip.

20. The method of claim 16, wherein a releasable liner is provided over the adhesive layer, which is removed prior to positioning the at least one conduit on the strip.

* * * * *